(12) United States Patent
Iwashita et al.

(10) Patent No.: US 9,050,381 B2
(45) Date of Patent: Jun. 9, 2015

(54) METHOD FOR STERILIZING SURFACE OF SPACE AND STERILIZATION SYSTEM

(75) Inventors: Takeshi Iwashita, Yokohama (JP); Miki Hirabayashi, Yokohama (JP)

(73) Assignee: TOYO SEIKAN KAISHA, LTD., Tokyo (JP)

( * ) Notice: Subject to any disclaimer, the term of this patent is extended or adjusted under 35 U.S.C. 154(b) by 458 days.

(21) Appl. No.: 13/522,811

(22) PCT Filed: Oct. 15, 2010

(86) PCT No.: PCT/JP2010/068111
§ 371 (c)(1),
(2), (4) Date: Jul. 18, 2012

(87) PCT Pub. No.: WO2011/089765
PCT Pub. Date: Jul. 28, 2011

(65) Prior Publication Data
US 2012/0288406 A1    Nov. 15, 2012

(30) Foreign Application Priority Data
Jan. 22, 2010  (JP) .................................. 2010-012556

(51) Int. Cl.
*A61L 2/18*     (2006.01)
*A61L 9/14*     (2006.01)
*B29C 49/42*    (2006.01)
*B65B 55/10*    (2006.01)

(52) U.S. Cl.
CPC ............... *A61L 9/14* (2013.01); *A61L 2209/14* (2013.01); *A61L 2209/211* (2013.01); *B29C 49/4252* (2013.01); *B65B 55/10* (2013.01)

(58) Field of Classification Search
CPC .......... B65B 55/10; B65B 55/12; B65B 55/18
USPC ......................................................... 422/28
See application file for complete search history.

(56) References Cited

U.S. PATENT DOCUMENTS 4,296,068 A      10/1981 Hoshino
6,120,730 A *    9/2000 Palaniappan et al. ............ 422/28

(Continued)

FOREIGN PATENT DOCUMENTS

JP    55-110555 A      8/1980
JP    01-267131 A     10/1989

(Continued)

OTHER PUBLICATIONS

Translation of JP 04-030783.*

(Continued)

*Primary Examiner* — Kevin Joyner
(74) *Attorney, Agent, or Firm* — Westerman, Hattori, Daniels & Adrian, LLP (57) ABSTRACT

Provided are a method and a device for sterilizing the surface of a space-to-be-sterilized which are safe to the human body, which are effective even for sterilizing spore-forming bacteria, which do not require the space-to-be-sterilized to be highly shielded, and which can sterilize the surface of the space efficiently with inexpensive equipment. The disclosed method involves: spraying a low-concentration sterilizing agent in the form of fine particles into the space-to-be-sterilized and making the sterilizing agent adhere to the surface thereof, the low-concentration sterilizing agent being any one of a 1-10 wt % aqueous solution of hydrogen peroxide, a 0.1-1 wt % aqueous solution of peracetic acid, or a 0.01-0.1 wt % aqueous solution of hypochlorous acid; adjusting the humidity in the space-to-be-sterilized; and air-drying the sterilizing agent. Thus, a high level of sterilization can be achieved in a short time and at low cost.

9 Claims, 2 Drawing Sheets

(56) References Cited

U.S. PATENT DOCUMENTS

| | | | |
|---|---|---|---|
| 6,984,360 B1 * | 1/2006 | Feuilloley et al. | 422/28 |
| 2009/0081326 A1 | 3/2009 | Adriansens et al. | |
| 2010/0047120 A1 * | 2/2010 | Adriansens et al. | 422/22 |

FOREIGN PATENT DOCUMENTS

| | | |
|---|---|---|
| JP | 04-030783 A | 2/1992 |
| JP | 05-065148 A | 3/1993 |
| JP | 2002-193220 A | 7/2002 |
| JP | 2006-248617 A | 9/2006 |
| JP | 2006-288624 A | 10/2006 |
| JP | 2006-288647 A | 10/2006 |
| JP | 2008-543619 A | 12/2008 |

OTHER PUBLICATIONS

International Search Report for PCT/JP2010/068111, mailing date of Nov. 16, 2010.

* cited by examiner

METHOD FOR STERILIZING SURFACE OF SPACE AND STERILIZATION SYSTEM

TECHNICAL FIELD

The present invention relates to a method and a system for sterilizing, using a sterilizing agent, the surface of a space that requires sterilization or cleaning, such as a plant for production of medicines and containers such as hygienic bottles for an aseptic filling line for beverages, food, and the like.

BACKGROUND ART

In plants for production of medicines and containers such as hygienic bottles for aseptic filling with beverages, food, and the like, the surface of production equipment that comes into direct or indirect contact with the containers or products, or the surface of the containers, or the inner surface of a space (called collectively hereinbelow as "the surface of a space-to-be-sterilized") requires a high level of cleaning at all times. The techniques, whether conventional or novel, for sterilizing the surface of a space-to-be-sterilized are particularly indispensable in production of containers such as hygienic bottles for aseptic filling. A variety of methods have been suggested for such sterilization, but a definitive technique has not yet been developed, and the sterilization remains one of the important technological tasks that should be contested at the production site. The reason therefor is that the technique for sterilizing the surface of a space-to-be-sterilized appears, while appearing to be simple at a first glance, should take into account: (1) the selection of a suitable sterilizing agent corresponding to the type of bacteria to be sterilized, so that the desired bactericidal effect is obtained; (2) the effect on the health of workers and the environment; (3) the cost of sterilization equipment; (4) the cost of human labor; (5) the effect produced on efficiency of production line, such as sterilization time; and (6) the effect produced on the products, and all of the aforementioned conditions should be satisfied. However, the conventional techniques for sterilizing the surface of a space-to-be-sterilized have both merits and demerits, and the method satisfying all of the conditions has not yet been suggested.

Where the conventional techniques are examined from the standpoint of the aforementioned conditions (1) to (6), one of the methods for sterilizing the surface of a space-to-be-sterilized includes impregnating a cloth or the like with a sterilizing agent such as alcohol and wiping with the cloth. However, the problem associated with alcohol sterilizing agents is that although such agents are effective for general sterilization, they are not effective against spore-forming bacteria, and for some sterilization objects, a problem is associated with the aforementioned condition (1). Further, with such a method, a long time is required for wiping in the case of a wide space and the cost of human labor rises. Meanwhile, the surface of a very narrow space is difficult to wipe sufficiently and problems are also associated with the conditions (4) and (5).

Aqueous solutions of hydrogen peroxide or aqueous solutions of peracetic acid have been used as sterilizing agents against spore-forming bacteria. A 35% aqueous solution of hydrogen peroxide is typically used as hydrogen peroxide for surface sterilization, and the following sterilization methods have been suggested: a method by which a 35% aqueous solution of hydrogen peroxide and sterilized air are sprayed from a two-fluid nozzle inside an aseptic chamber, then heated sterilized air is fed in for 30 minutes, and the sterilizing agent is removed by evaporation (Patent Document 1), a method by which a 35% aqueous solution of hydrogen peroxide is gasified and condensed to obtain hydrogen peroxide mist which is forcibly introduced into a chamber and agitated (see Patent Documents 2 to 4), and a method by which a space to be treated is filled with gasified aqueous solution of hydrogen peroxide (Patent Documents 5 and 6).

However, since an aqueous solution of hydrogen peroxide with a high concentration of 35% is used, where such solution gets on the skin, a severe burn occurs. Hence, it is necessary to wear protective clothing, protective eyeglasses, and a mask and wait till the sprayed solution is dried. Therefore, in this case, problems are associated with the conditions (2) and (5). Furthermore, in order to ensure sufficient contact of the gasified sterilizing agent with the sterilization object surface and prevent the sterilizing agent from leaking to the outside, airtight space equipment with high-level shielding of the space-to-be-sterilized is required. In addition, a waste gas treatment apparatus is required for detoxifying the waste gas, huge investment in equipment is required and problems are associated with the aforementioned condition (3). Accordingly, a variety of methods for sterilizing the surface of a space-to-be-sterilized have been suggested that involve such sterilization by gasification of a sprayed sterilizing agent as described above, but since a high-cost equipment is required for protection against the gasified high-concentration sterilizing agent, practically none of such methods has been put to practical use, and a method by which an aqueous solution of a sterilizing agent is directly injected or sprayed on the sterilization object and then washed with aseptic water has been generally used for sterilizing a space with chemical agents. However, such a method is not suitable for sterilization objects that are adversely affected by wet conditions. Other problems include low sterilization efficiency and the necessity to use large amounts of the sterilizing agent and washing water. Furthermore, when a sterilizing agent is simply applied and then naturally dried, a long time is required for complete removal thereof and problems are associated with the aforementioned conditions (5) and (6).

PRIOR ARTS

Patent Documents

Patent Document 1: Japanese Patent Application Publication No. H1-267131
Patent Document 2: Japanese Patent Application Publication No. H5-65148
Patent Document 3: Japanese Patent Application Publication No. 2002-193220
Patent Document 4: Japanese Patent Application Publication No. 2006-248617
Patent Document 5: Japanese Patent Application Publication No. 2006-288647
Patent Document 6: Japanese Patent Application Publication No. 2006-288624

DISCLOSURE OF THE INVENTION

Problem to be Solved by the Invention

Accordingly, it is an object of the present invention to provide a method for sterilizing a surface of a space-to-be-sterilized, that can resolve the abovementioned problems (1) to (5) associated with the conventional methods for sterilizing the surface of a space-to-be-sterilized, and more particularly to provide a method and a system for sterilizing the surface of a space-to-be-sterilized which shorten the sterilization time and reduce the labor, ensure safety to a human body and effectiveness in sterilization of spore-forming bacteria, do not require an expensive apparatus for gasification of aqueous solution of hydrogen peroxide, do not require high-level shielding of the space-to-be-sterilized or huge investment in equipment and enable efficient sterilization of the surface of space-to-be-sterilized with inexpensive equipment.

The results of the comprehensive study conducted by the inventors to resolve the aforementioned problems demonstrate that by atomizing a low-concentration sterilizing agent, which has not been considered suitable for use in the conventional methods for sterilizing the surface of a space-to-be-sterilized, making the sterilizing agent adhere to the surface of the space-to-be-sterilized, and drying (air-drying), it is possible to perform the sterilization safely, in a short time, and with the same bactericidal effect as in the case of the conventional high-concentration sterilizing agent. This finding led to the creation of the present invention.

Thus, the method for sterilizing the surface of a space in accordance with the present invention that resolves the aforementioned problems includes atomizing a sterilizing agent adjusted to a low concentration, spraying the atomized sterilizing agent into the space-to-be-sterilized, making the sterilizing agent adhere to the surface thereof, and then drying the sterilizing agent.

In accordance with the present invention, the sterilizing agent adjusted to a low concentration is atomized, caused to adhere to the surface of a sterilization object in the space-to-be-sterilized, and dried, thereby making it possible to sterilize the surface of the space-to-be-sterilized without adversely affecting the human body even in direct contact therewith, with a little effect on environment, and without the necessity to shield the space-to-be-sterilized and make it air tight.

Any of an aqueous solution of hydrogen peroxide with a concentration of 1 to 10 wt %, an aqueous solution of peracetic acid with a concentration of 0.1 to 1 wt %, or an aqueous solution of hypochlorous acid with a concentration of 0.01 to 0.1 wt % can be used as the low-concentration sterilizing agent. In the case of the conventional sterilizing agents for sterilizing the surface of a space, for example, an aqueous solution of hydrogen peroxide has a concentration of 35%, whereas, the present invention enables space sterilization at an incomparably low concentration. The sterilizing agent is desirably atomized by mixing the sterilizing agent with air at normal temperature. For example, the atomization at normal temperature can be achieved by an atomization method using a gas-liquid two-fluid spraying nozzle or an atomization method using ultrasound vibrations. In the atomization of the sterilizing agent, the average particle size is 1 to 500 μm, preferably 1 to 100 μm, and more preferably 1 to 30 μm. Where the average particle size is less than 1 μm, it is difficult to make the particles adhere to the surface that is the sterilization object and no bactericidal effect is obtained. Where the average particle size is more than 500 μm, locations appear in which the particles are connected to each other and form a film and the sterilizing agent is difficult to dry in such locations. As a result, the bactericidal effect cannot be increased, leading to an unfavorable result.

The sterilizing agent is preferably dried by the so-called air-drying process which is performed under a positive-pressure atmosphere by blowing air. By drying under a positive-pressure atmosphere, it is possible to prevent bacteria from flowing from the outside into the space-to-be-sterilized, and drying can be performed efficiently in a short period of time, without producing a thermal effect on the surface to be sterilized. Further, by forcibly drying the sterilizing agent that has adhered to the surface of the sterilization object, it is possible to increase the bactericidal effect by comparison with that in the case of natural drying of the adhered sterilizing agent, a high bactericidal effect is demonstrated even at a low concentration, and even the pore-forming bacteria can be sterilized in a short time.

It is preferred that the sterilized air be used for drying the surface of the space-to-be-sterilized. With some types of the space-to-be-sterilized and bacteria which are the sterilization objects, the air to be used for drying is not required to be sterilized, but by using the sterilized air, it is possible to minimize the inflow of new contaminating bacteria from the outside.

The adhered amount of the sterilizing agent at the surface of the space-to-be-sterilized is preferably 1 to 3 mg/cm$^2$. By so making the appropriate amount of sterilizing agent adhere to the surface of the space-to-be-sterilized, it is possible to increase the bactericidal effect more effectively.

In order to perform effective drying of the sterilizing agent on the surface of the space-to-be-sterilized, it is preferred that the humidity and temperature of the space-to-be-sterilized and the drying time be adjusted. By adjusting the humidity and temperature of the environment surrounding the space-to-be-sterilized, it is possible to accelerate the drying of the surface of the space-to-be-sterilized. For example, in the manufacture of containers such as the aforementioned hygienic bottles, in the case of products that require a dry state, as in the case of sterilizing the preforms supplied to blow molding or sterilizing the stretch-blow molding process, the drying of the surface of the space-to-be-sterilized is accelerated, the products are conveyed to the next step in the dry state, and more effective production is realized. It is preferred that the humidity of the space-to-be-sterilized be adjusted to 20 to 60% RH, the temperature be adjusted to 25 to 50° C., and the drying time be adjusted within a range of 5 to 60 minutes; the correlation of the conditions is described hereinbelow in test examples. Such adjustments make it possible to obtain the appropriate bactericidal effect, shorten the sterilization time, and increase the efficiency of sterilization, in particular, in the production line.

In the case where the surface of the space-to-be-sterilized is the surface of a line for supplying preforms for stretch-blow molding of bottles and the surface of products and equipment in a stretch-blow molding process referred to as stretch-blow molding, preform sterilization and hygienic bottle production can be performed, and beverages or the like of such hygienic bottles can be supplied in an on-line mode to an aseptic filling line.

A sterilization system for the surface of a space in accordance with the present invention that resolves the aforementioned problems includes atomization means (denoted by the reference numeral 3 in FIG. 1) for atomizing a sterilizing agent to be sprayed into a space-to-be-sterilized, aseptic means for sterilizing external air supplied into the space-to-be-sterilized, and air conditioning means for controlling humidity and temperature of the space-to-be-sterilized, wherein the sterilizing agent that has been atomized by the atomization means is dried under a positive-pressure atmosphere. The positive-pressure atmosphere condition is preferably 1 to 100 pa. With the sterilization system for a surface of a space in accordance with the present invention, the surface of a space can be reliably and effectively sterilized using inexpensive equipment.

By providing discharge gas treatment means between the space-to-be-sterilized and the air conditioning means, it is possible to control easily the positive pressure determined by the external air in the space-to-be-sterilized and the concentration of the sterilizing agent. Where the discharge gas treatment means has sterilizing agent decomposition means, the sterilizing agent discharged from the space-to-be-sterilized can be decomposed and removed, discharged into the atmosphere, or circulated through the air conditioning means and supplied to the space-to-be-sterilized.

By providing the aseptic means for sterilizing external air supplied into the space-to-be-sterilized with atomization means (denoted by the reference numeral 4 in FIG. 1 described later) for atomizing the sterilizing agent, and spraying the sterilizing agent into the aseptic means, it is possible to maintain easily the sterilization state of the aseptic means. By providing purification means for purifying the external air supplied to the atomization means (denoted by the reference numerals 3 and 4 in FIG. 1), it is possible to further increase the level of sterilization of the sterilizing agent sprayed into the space-to-be-sterilized and/or the aseptic means for sterilizing the external air supplied into the space-to-be-sterilized. Where the atomization means is in the form of a two-fluid spraying nozzle for the sterilizing agent and air, the sterilizing agent can be easily atomized and made adhere to the surface of the space.

Effect of the Invention

With the method for sterilizing the surface of a space in accordance with the present invention, the number of workers and operations can be greatly reduced by comparison with that of the conventional ethanol wiping sterilization method and a bactericidal effect equal to or greater than 2D is also demonstrated with respect to pore-forming bacteria that cannot be sterilized by alcohol sterilization. Furthermore, a sufficient bactericidal effect can be obtained at a low concentration that is much lower than the conventional sterilizing agent concentration, and the aforementioned problems occurring when a high-concentration sterilizing agent is used can be entirely resolved. Thus, since a sterilizing agent with a very low concentration can be used, the cost of the sterilizing agent can be accordingly reduced, the effect on human body and environment can be reduced, handleability is improved, the investment in equipment for forming a sealed space for shielding the circulation of the external air, which has conventionally been the most serious problem, is not required, and simple equipment can be used. In addition, air-drying can be employed as a drying method, and by performing the air-drying under a positive pressure, it is possible to perform drying while preventing the inclusion of new contaminating bacteria from the outside.

With the system for sterilizing the surface of a space in accordance with the present invention, it is possible to sterilize the surface of the space efficiently and reliably with inexpensive equipment.

EXPLANATION OF REFERENCE NUMERALS 1 sterilization object
2 space-to-be-sterilized
3 first two-fluid spraying nozzle
4 second two-fluid spraying nozzle
5 filter unit (aseptic means)
6 air conditioning means
7 discharge gas treatment means
8 cartridge filter (purification means)
10 air supply passage
11 passage for supplying aqueous solution of sterilizing agent
12, 13, 14 air circulation paths
12-1, 12-2 branching paths

BEST MODE FOR CARRYING OUT THE INVENTION

Embodiments of the method for sterilizing the surface of a space and the system for sterilizing the surface of a space in accordance with the present invention will be explained below in greater detail with reference to the appended drawings.

Figure 1:
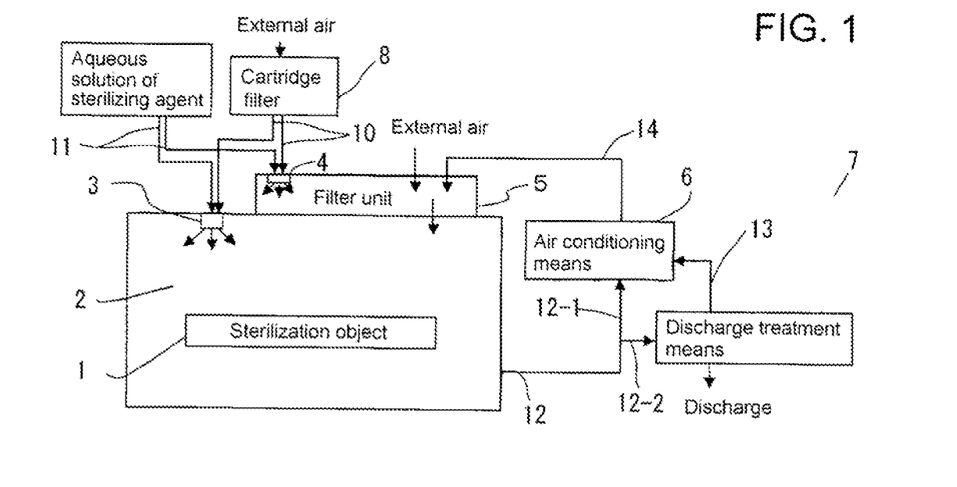
FIG. 1 is a schematic diagram of the apparatus using the method for sterilizing the surface of a space in accordance with the present invention.

FIG. 1 is a block diagram illustrating the method for sterilizing the surface of a space and the system for sterilizing the surface of a space in accordance with the present invention.

The present system includes first atomization means for atomizing a sterilizing agent that is sprayed into a space-to-be-sterilized, aseptic means for sterilizing the external air supplied into the space-to-be-sterilized, and air conditioning means for controlling the temperature and humidity in the space-to-be-sterilized. The specific feature of the system is that the sterilizing agent that has been atomized by the first atomization means and adhered to the surface of the space is dried under a positive-pressure atmosphere of the space-to-be-sterilized. The system for sterilizing the surface of a space includes a sterilizing agent spraying step and a sterilizing agent drying and sterilization step.

In the sterilizing agent spraying step, a low-concentration aqueous solution of a sterilizing agent is atomized and sprayed from a two-fluid spraying nozzle 3, which is the first atomization means for atomizing the sterilizing agent, around (non-sealed state) of a space-to-be-sterilized 2 in which a sterilization object 1, such as a device, is disposed. For example, the conventional air-assist inner-mixing spray nozzle can be used as the aforementioned two-fluid spraying nozzle 3. The nozzle is connected to an air (external air) supply path 10 and a path 11 for supplying an aqueous solution of the sterilizing agent. The aqueous solution of the sterilizing agent and air supplied in a pressurized state are mixed and the aqueous solution of the sterilizing agent is atomized and sprayed. It is preferred that a plurality of such first two-fluid spraying nozzles 3 be disposed so as to ensure uniform spraying inside the space-to-be-sterilized though only one nozzle is shown in the figures. Further, it is also preferred that the first two-fluid spraying nozzles 3 have an automation function, that the angle thereof could be changed, and that the atomized particles of the sterilizing agent could be uniformly coated in the space-to-be-sterilized. Further, it is preferred that the air (external air) supplied to the first two-fluid spraying nozzles 3 be purified by a filter such as a cartridge filter 8, which is purification means.

In the sterilizing agent drying and sterilization step, the external air (air) is supplied into the space-to-be-sterilized 2; this step is implemented using a filter unit 5, air conditioning means 6, and discharge gas treatment means 7 disposed outside the space-to-be-sterilized 2.

The external air (air) used for drying and sterilization is supplied to the space-to-be-sterilized 2 through the filter unit 5, which is aseptic means. The filter unit 5 is preferably a combination of filter layers constituted by a pre-filter, a medium-performance filter, and a high-performance filter, or a pre-filter, a medium-performance filter, and an ultrahigh-performance filter arranged in the order of description from the outer layer side though this configuration is not shown in the figure. The air is sterilized when passing through these filter layers and enters the space-to-be-sterilized 2. In the present embodiment, a second two-flow spraying nozzle 4, which is second atomization means for atomizing the sterilizing agent and is similar to the two-flow-spraying nozzle 3, which is the above-described first atomization means, is disposed on the surface of the upper portion of the filter unit 5 that is in contact with the air inlet surface of the filter of the outermost layer, from among the aforementioned filter layers, and this second two-fluid spraying nozzle is used to atomize the sterilizing agent and spray the atomized sterilizing agent on the outermost filter. It is preferred that a plurality of such second two-fluid spraying nozzles 4 be disposed in order to spray evenly the sterilizing agent for sterilization. By sterilizing the filter of the outermost layer in the above-described manner, it is possible to prevent the filter unit 5 from contamination with bacteria from the external air.

Air circulation paths 12, 13, 14 by which the air is supplied into the space-to-be-sterilized 2 through the filter unit 5 are formed, as shown in FIG. 1, between the filter unit 5, space-to-be-sterilized 2, air conditioning means 6, and discharge gas treatment means 7. The circulation path 12 is branched into a branched path 12-1 extending from the space-to-be-sterilized 2 and communicating with the air conditioning means 6 and the branch path 12-2 communicating with the discharge gas treatment means 7. The air supplied into the space-to-be-sterilized 2 through the filter unit 5 can be selectively fed and circulated, as will be described hereinbelow, to the air conditioning means 6 and the discharge gas treatment means 7 through the circulation paths 12, 13, 14.

The air conditioning means 6 has a function of controlling humidity and temperature and also blowing air, and the discharge gas treatment means 7 has a function of controlling the ratio of the discharge amount to the inlet amount of the air supplied into the space-to-be-sterilized 2 and also the pressurization in the space-to-be-sterilized 2 and a function of controlling the concentration of the sterilizing agent in the air. The discharge gas treatment means 7 is disposed so as to communicate with the space-to-be-sterilized 2 and the air conditioning means 6 and preferably has sterilizing agent decomposition means for decomposing and removing the sterilizing agent located in the air. When the sterilizing agent decomposition means is present, the sterilizing agent located in the air discharged from the space-to-be-sterilized 2 is decomposed, removed and discharged into the atmosphere or supplied into the space-to-be-sterilized via the circulation paths 13, 14 through the air conditioning means 6 and the filter unit 5. For example, well-known sterilizing agent decomposition means for decomposing and removing the sterilizing agent contained in the air, such as means in which a metal is mixed as a catalyst with ceramic, can be used as the aforementioned sterilizing agent decomposition means.

It is preferred that the external air (air) be introduced through the filter unit 5 immediately after the sterilizing agent has been sprayed to start the drying and sterilization step. By supplying the air after the sterilizing agent has been sprayed, it is possible to spray the sterilizing agent evenly into the space-to-be-sterilized 2, the spraying being unaffected by the air. When the concentration of the sterilizing agent in the space-to-be-sterilized 2 is high, it is preferred that the air be returned from the discharge gas treatment means 7 into the filter unit 5 through the air conditioning means 6 and introduced for drying and sterilizing the space-to-be-sterilized 2 again. By using such a path, it is possible to use the filter layer longer and therefore the running cost can be reduced by comparison with the case where the external air (air) is introduced and discharged at all times. Further, in order to reduce the running cost of the sterilizing agent decomposition means of the discharge gas treatment means 7, it is preferred that the air be circulated from the space-to-be-sterilized 2 only to the air conditioning means. In this case, it is also preferred that the air pass through the discharge gas treatment means 7 before the drying and sterilization step is completed. Therefore, the combination of air circulation paths relating to the space-to-be-sterilized in the present system includes the following three paths: (1) space-to-be-sterilized 2→discharge gas treatment means 7→air conditioning means 6→filter unit 5→space-to-be-sterilized 2; (2) space-to-be-sterilized 2→air conditioning means 6→filter unit 5→space-to-be-sterilized 2, and (3) space-to-be-sterilized 2→discharge gas treatment means 7→discharge. In the sterilizing agent spraying step, all these circulation paths are stopped, and in the drying and sterilization step, these paths are combined as appropriate to control the circulation and discharge of the air, thereby making it possible to perform drying and sterilization of the space-to-be-sterilized more efficiently. When the discharge gas treatment means has sterilizing agent decomposition means, the space-to-be-sterilized 2 may be sealed.

It is further preferred that the air (external air) supplied to the first two-fluid spraying nozzle 3 and the second two-fluid spraying nozzle 4 be purified through the filter of the cartridge filter 8 which is purification means. In such a case, it is possible to achieve a higher level of sterilization of the filter unit 5 which is aseptic means for the sterilizing agent sprayed into the space-to-be-sterilized 2 and the external air supplied into the space-to-be-sterilized 2.

Any method by which the sterilizing agent and air can be mixed and the mixture can be caused to adhere, such as an atomization method using ultrasonic vibrations, can be used instead for the two-fluid spraying nozzles for atomizing the sterilizing agent. With certain types of environment in the space-to-be-sterilized 2 and bacteria which are the object of sterilization, it is not necessary to sterilize the air used for drying. In this case, the filter unit 5 or the cartridge filter 8 is unnecessary.

In another embodiment of the method for sterilizing the surface of a space in accordance with the present invention, the sterilizing agent may be also sprayed into the space-to-be-sterilized by using a miniaturized sterilizing agent spraying apparatus which is provided with a mechanism that takes in an aqueous solution of a sterilizing agent and air (external air) and in which the sterilizing agent is sprayed with a two-fluid spraying nozzle. By using such a miniaturized sterilizing agent spraying apparatus, it is possible to perform sterilization that is flexibly adapted to the surface that is the object of sterilization inside the space-to-be-sterilized.

TEST EXAMPLE

Test Example 1

The inventors have conducted the following tests to verify the relationship between the concentration of an aqueous solution of hydrogen peroxide and the bactericidal effect in the method for sterilizing the surface of a space by the method in which the aqueous solution of hydrogen peroxide is sprayed and then evaporated and dried.

Figure 2:
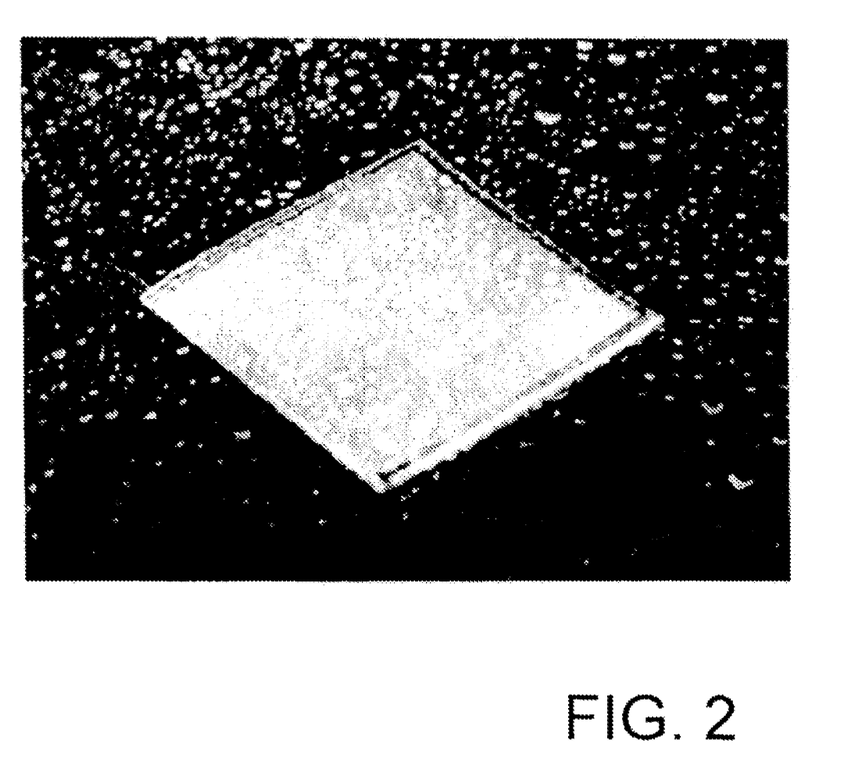
FIG. 2 is an enlarged photo illustrating the state in which an aqueous solution of hydrogen peroxide is sprayed onto a test piece.

As shown in Table 1, six types of aqueous solutions of hydrogen peroxide with concentrations of 0.1 wt %, 0.3 wt %, 1 wt %, 3 wt %, 10 wt %, and 30 wt %, were prepared. Sample bacteria *Bacillus subtilis* were planted and dried on one surface of a 10 mm×10 mm aluminum sheet to prepare a test piece, and the aforementioned prepared aqueous solutions of hydrogen peroxide were twice sprayed from a distance of 100 nm from the test piece with an atomizer and caused to adhere to the test piece. The diameter of fine particles of the sterilizing agent was within a range of 1 to 30 μm and the adhered amount of the sterilizing agent was 1 mg/cm$^2$. FIG. 2 shows an enlarged photo of the test piece on which the sterilizing agent is seen as grains. The observations demonstrate, as shown in FIG. 2, that the aqueous solution of hydrogen peroxide has uniformly adhered to the test piece in a right amount. The test piece was then air-dried for 30 minutes (till the dry state was visually confirmed) in a clean bench under an atmosphere at a temperature of 35° C. and a humidity of 60% RH. The test piece was then immersed in a dextrose tripton broth culture medium and cultured for 7 days at a temperature of 35° C. to confirm the bactericidal effect. The results are shown in Table 1.

TABLE 1

| Chemical agent | Chemical agent concentration (wt %) | Bactericidal effect equal to or higher than 2D |
|---|---|---|
| Hydrogen peroxide | 0.1 | X |
|  | 0.3 | X |
|  | 1 | ○ |
|  | 3 | ○ |
|  | 10 | ○ |
|  | 30 | ○ |

○: no bacteria remained
X: bacteria remained

The results of the present test example demonstrate that where the concentration of the aqueous solution of hydrogen peroxide is equal or higher than 1 wt %, a bactericidal effect equal to or higher than 2D (sterilization ratio 99%) can be confirmed with respect to *Bacillus subtilis* spores that are the test bacteria and sufficient sterilization suitable for practical use can be performed even though the concentration of the aqueous solution of hydrogen peroxide is not equal to or higher than a high concentration of 30 wt % which is typical for the conventional process. At a concentration of 0.1 wt % and 0.3 wt %, living bacteria remained and sufficient bactericidal effect was not observed.

Test Example 2

The following test for measuring the concentration of hydrogen peroxide gas in air-drying has been performed to confirm safety to workers during the sterilization by spraying of the aqueous solution of hydrogen peroxide.
Spraying location: work table of clean bench (manufactured by AIR TECH).
Blowing speed: about 0.45 m/sec.
Size: 1,260 mm×650 mm.
Hydrogen peroxide concentration: 3 wt %.
Test method: a 3 wt % aqueous solution of hydrogen peroxide was sprayed obliquely on the entire work table of the clean bench from a distance of 100 mm from the work table to obtain the adhere amount of 1 mg/cm$^2$ (the uniformly sprayed state of the sterilizing agent on the entire work table surface has been visually confirmed) and blow dried. A hydrogen peroxide concentration meter (manufactured by Dräger) was placed on the work table and the concentration of hydrogen peroxide gas in the atmosphere in the clean bench was recorded every 30 sec.
Drying conditions: drying (humidity 60% RH, temperature 28° C.) was conducted with the closed front door of the clean bench.

Figure 3:
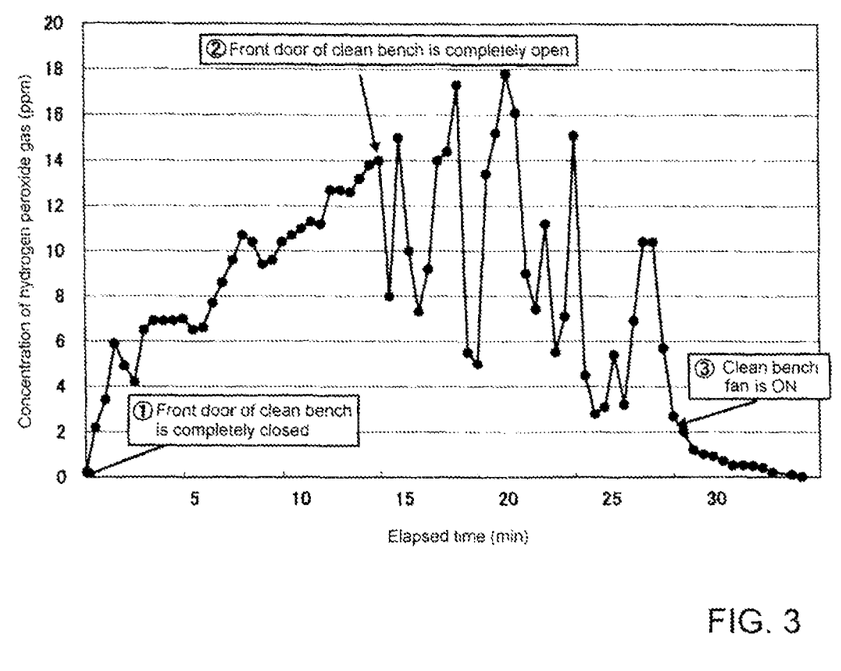
FIG. 3 is a graph illustrating the relationship between the hydrogen peroxide gas concentration in the atmosphere and the time elapsed in the air-drying test performed at a clean bench.

The results obtained in measuring the concentration of the hydrogen peroxide gas versus the time elapsed after the aqueous solution of hydrogen peroxide has been sprayed are shown in FIG. 3. The concentration of hydrogen peroxide gas in the atmosphere in the clean bench increased and decreased with time and became 0 ppm in 36 minutes after the spraying, thereby indicating almost complete drying. The "TWA (time weighted average allowed exposure limit)" suggested by ACGIH (American Conference of Governmental Industrial Hygienists) and OSHA (Occupational Safety & Health Administration) is 1 ppm, and because the concentration of the aqueous solution of hydrogen peroxide after drying in the present test is within the stipulated range, no adverse effect on human body is produced even in direct contact therewith.

Further, as shown in FIG. 3, the concentration of hydrogen peroxide gas in the atmosphere in the clean bench during drying increased to a maximum of 18 ppm. The "IDLH (Immediately Dangerous to Life and Health)" of hydrogen peroxide suggested by NIOSH (National Institute for Occupational Safety and Health (USA)) and OSHA (Occupational Safety & Health Administration) is 75 ppm, and the maximum concentration in the present test is equal to or less than ¼ of the IDLH. Even when the sprayed concentration of hydrogen peroxide is 10 wt %, the result is equal to or less than IDHL. However, in order to ensure safety, it is still preferred that you stay away from the spraying location during drying, and the protective gear such as a mask and protective glasses be used during spraying.

In addition, the concentration of hydrogen peroxide remaining after the aqueous solution of hydrogen peroxide has been sprayed and dried was confirmed. The spraying location was inside the clean bench under the same conditions as in Test Example 2, and the concentration of the sprayed aqueous solution of hydrogen peroxide was 10 wt %.

Remaining concentration measurement method: the sprayed aqueous solution of hydrogen peroxide was dried, 5 ml of ion exchange water was dropped on the work table (sprayed surface), and the concentration of the aqueous solution of hydrogen peroxide remaining in the ion exchange water was measured with a remaining hydrogen peroxide concentration meter (Reflectoquant).

The results are shown in Table 2.

TABLE 2

| Sprayed hydrogen peroxide concentration (wt %) | Dropped amount (ml) | Time elapsed after dropping (min) | Remaining concentration of hydrogen peroxide (ppm) |
|---|---|---|---|
| 10 | 5 | 0 | 0.1 |

As shown in Table 2, the concentration of hydrogen peroxide remaining on the sprayed surface after the 10 wt % aqueous solution of hydrogen peroxide has been sprayed and dried was 0.1 ppm. The FDA (USA) stipulates, as a reference for the residual amount of hydrogen peroxide, that hydrogen peroxide should not be present in a concentration equal to or higher than 0.5 ppm when the analysis is performed immediately after the distilled water has been filled and sealed under the production conditions. Therefore, the present results satisfy this condition.

The results relating to the hydrogen peroxide concentration during spraying/after drying have confirmed that with the present test, even when the sterilization is performed using a 10 wt % aqueous solution of hydrogen peroxide, no adverse effect is produced on human body and the process is safe even when the sterilization environment is not tightly sealed, provided that no person enters the drying and sterilization environment.

Test Example 3

A test has been conducted to confirm the effective concentration for obtaining the bactericidal effect by using different chemical agents.

Sprayed liquids: aqueous solution of hydrogen peroxide, aqueous solution of peracetic acid, and aqueous solution of sodium hypochlorite.

Test bacteria: *Bacillus subtilis*.

Method: The test bacteria were planted and dried on one side of a 10 mm×10 mm aluminum sheet (test piece). Each of the aforementioned chemical agents was sprayed on the respective test piece to obtain the adhered amount of 1 mg/cm$^2$ and dried. The test species were then immersed into a culture medium and cultured. The drying state of the chemical agents was visually confirmed.

Drying conditions: drying (humidity 60% RH, temperature 25° C.) was conducted with the closed front door of the clean bench.

Drying time: 30 minutes.

Culturing conditions: dextrose tripton broth culture medium, culturing at 35° C.

The results are shown in Table 3.

TABLE 3

| | Hydrogen peroxide concentration (wt %) | | | |
|---|---|---|---|---|
| Chemical agent | 0.3 | 1 | 5 | 10 |
| Hydrogen peroxide | X | ○ | ○ | ○ |

| | Peracetic acid concentration (wt %) | | | |
|---|---|---|---|---|
| Chemical agent | 0.01 | 0.1 | 0.5 | 1 |
| Peracetic acid | X | ○ | ○ | ○ |

| | Hypochlorous acid concentration (wt %) | | | |
|---|---|---|---|---|
| Chemical agent | 0.001 | 0.01 | 0.05 | 0.1 |
| Hypochlorous acid | X | ○ | ○ | ○ |

○: 99% killed
X: 99% not killed

The results of the present test example have confirmed that the desired sterilization results are obtained at a chemical agent concentration of 1 to 10 wt % in the case of an aqueous solution of hydrogen peroxide, 0.1 to 1 wt % in the case of an aqueous solution of peracetic acid, and 0.01 to 0.1 wt % in the case of an aqueous solution of hypochlorous acid.

With consideration for further reduction of adverse effect on human body and decrease in the amount of the chemical agent, it is preferred that the aqueous solution of hydrogen peroxide have a concentration within a range of 1 to 5 wt %, an aqueous solution of peracetic acid have a concentration within a range of 0.1 to 0.5 wt %, and an aqueous solution of hypochlorous acid have a concentration within a range of 0.01 to 0.05 wt %.

Concerning the aqueous solution of hydrogen peroxide, where the concentration is more than 6 wt %, it corresponds to a "Non-medicinal Deleterious Substance". This is one more reason why it is preferred that the concentration be adjusted to a low level of equal to or less than 5 wt %.

Test Example 4

The relationship between the concentration of the sterilizing agent, amount of the adhered sterilizing agent, bactericidal effects and drying state was confirmed.

Sterilizing agent: aqueous solution of hydrogen peroxide (concentration: 1 wt %, 3 wt %, 5 wt %, and 10 wt %).

Test bacteria: *Bacillus subtilis*.

Method: The test bacteria were planted on one side of a 10 mm×10 mm aluminum sheet (test piece). Spraying was performed by changing the amount of the chemical agent adhered to the test piece. The drying was performed by changing the drying time and the test species were then immersed into a culture medium and cultured. The drying state of the chemical agents was visually confirmed.

Drying conditions: drying (humidity 60% RH, temperature 25° C.) was conducted with the closed front door of the clean bench.

Culturing conditions: dextrose tripton broth culture medium, culturing at 35° C.

The results are shown in Table 4.

TABLE 4

| Chemical agent | Chemical agent concentration (wt %) | Item | Amount adhered (mg/cm$^2$) | Drying time (min) | | | |
|---|---|---|---|---|---|---|---|
| | | | | 10 | 20 | 30 | 60 |
| Hydrogen peroxide | 1% | Bactericidal effect | 1 | X | X | ○ | ○ |
| | | | 3 | X | X | ○ | ○ |
| | | | 10 | X | X | X | X |
| | | Drying state | 1 | XX | XX | □ | □ |
| | | | 3 | XX | XX | □ | □ |
| | | | 10 | XX | XX | XX | XX |
| | 3% | Bactericidal effect | 1 | X | ○ | ○ | ○ |
| | | | 3 | X | X | ○ | ○ |
| | | | 10 | X | X | X | X |
| | | Drying state | 1 | XX | □ | □ | □ |
| | | | 3 | XX | XX | □ | □ |
| | | | 10 | XX | XX | XX | XX |
| | 5% | Bactericidal effect | 1 | X | ○ | ○ | ○ |
| | | | 3 | X | X | ○ | ○ |
| | | | 10 | X | X | X | X |
| | | Drying state | 1 | XX | □ | □ | □ |
| | | | 3 | XX | XX | □ | □ |
| | | | 10 | XX | XX | XX | XX |
| | 10% | Bactericidal effect | 1 | X | ○ | ○ | ○ |
| | | | 3 | X | X | ○ | ○ |
| | | | 10 | X | X | X | X |
| | | Drying state | 1 | XX | □ | □ | □ |
| | | | 3 | XX | XX | □ | □ |
| | | | 10 | XX | XX | XX | XX |

Bactericidal effect:
○: 99% killed
X: 99% not killed

Drying state:
□: dried
XX: not dried

According to Test Example 4, as clearly follows from Table 4, for all of the chemical agent concentrations (1 wt %, 3 wt %, 5 wt %, and 10 wt %), the chemical agent that has adhered at 1 mg/cm$^2$ and 3 mg/cm$^2$ was dried for 30 minutes of drying time and 99% of the test bacteria were dead. However, where the adhered amount was 10 mg/cm$^2$, the chemical agent was not dried within 30 minutes and the bactericidal effect rather decreased. This result suggests that the bactericidal effect strongly depends on the drying state and where the amount of the adhered chemical agent is large, but the chemical agent has not dried and remained wet, the bactericidal effect does not increase. Therefore, it is clear that the chemical agent should be caused to adhere in an appropriate amount and dried in order to increase the bactericidal effect.

In the present test example, 99% of the test bacteria, which are spore-forming bacteria, could be killed and the surface of the object of sterilization could be dried by spraying the aqueous solutions of hydrogen peroxide at a low concentration of 1 to 10 wt % and drying for 30 minutes at a very small adhered amount of the chemical agent of 1 to 3 mg/cm$^2$. These results have confirmed that a bactericidal effect can be demonstrated at a small adhered amount with the chemical agent at a low concentration that does not adversely affect human body or environment and that drying can be performed in a short time period of 30 minutes.

Test Example 5

In order to confirm the effect produced by the humidity in the space-to-be-sterilized on the drying state of the surface of the space, the drying state was confirmed by using an aqueous solution of hydrogen peroxide with a concentration of 1 wt % and changing the adhered amount and humidity.

Method: an aqueous solution of hydrogen peroxide with a concentration of 1 wt % was sprayed and dried on one side of a 10 mm×10 mm aluminum sheet (test piece). The drying state was visually confirmed.

Drying conditions: drying (temperature 28° C.) was conducted with the closed front door of the clean bench.

Drying time: 30 minutes.

The results are shown in Table 5.

TABLE 5

| Humidity (% RH) | Adhered amount (mg/cm$^2$) | | |
| --- | --- | --- | --- |
| | 1 | 3 | 10 |
| 20 | □ | □ | xx |
| 40 | □ | □ | xx |
| 60 | □ | □ | xx |
| 80 | xx | xx | xx |

□: dried
xx: not dried

The results obtained in Test Example 5 demonstrate that there is a correlation between the humidity of the space and the drying state of the sterilizing agent. The lower the humidity, the easier it is for the sterilizing agent to dry, and the humidity should be adjusted to 20 to 60% RH in order to dry within 30 minutes the sterilizing agent that has adhered at 1 to 3 mg/cm$^2$, as described in Test Example 4. Therefore, it has been confirmed that in the case of the adhered amount of 1 to 3 mg/cm$^2$, it is preferred that the humidity be maintained equal to or less than 60%.

Further, from the standpoint of energy efficiency, it is preferred that the temperature be 25 to 50° C., more preferably 25 to 35° C. at which no temperature adjustment is required even in a space in which heat is mechanically generated, as in a production line of containers and the like. In order to perform sufficient drying and obtain the bactericidal effect and also in order to avoid excess energy consumption on drying, it is preferred that the drying time be 5 to 60 minutes. Test Example 4 has confirmed that in a space with a humidity of 60% RH and a temperature of 25° C., where the adhered amount of the sterilizing agent is 1 mg/cm$^2$, the sterilizing agent is dried within 20 minutes and the bactericidal effect is obtained. However, when it is wished to shorten the drying time, the drying conditions of the sterilizing agent may be combined as appropriate, for example, by adjusting the humidity to a lower value and the temperature to a higher value, for example, such that the humidity of the space-to-be-sterilized is equal to or less than 20% RH and the temperature rises to 40 to 50° C.

By adjusting the aforementioned humidity, temperature, and drying time as appropriate, it is possible to obtain a high bactericidal effect even when a low-concentration sterilizing agent is used.

The confirmation in the aforementioned Test Examples 4 and 5 was obtained by using only the aqueous solution of hydrogen peroxide as the chemical agent, but when the aqueous solution of peracetic acid and aqueous solution of hypochlorous acid were used, the concentration of each chemical agent was even lower than that of the aqueous solution of hydrogen peroxide and the solutions were close to water, as shown in Table 3. Therefore, it is clear that the drying trend will be the same. Further, when an aqueous solution of peracetic acid is used, hydrogen peroxide is sometimes coexistent because of the nature of the production process.

In the method for sterilizing the surface of a space in accordance with the present invention, where a sterilizing agent adjusted to a low concentration is atomized, sprayed and caused to adhere to the space-to-be-sterilized, where the space-to-be-sterilized has a complex shape, a method by which the low-concentration sterilizing agent is immersed in a cloth and the like and the space-to-be-sterilized is wiped with the cloth can be additionally used to increase the bactericidal effect, and such applied sterilizing agent may be dried.

Further, in the aforementioned method for sterilizing the surface of a space in accordance with the present invention, when the surface of the space is that of a supply line for preforms for stretch-blow molding of bottles or products and equipment in the stretch-blow molding process, such as preform heating, stretch-blow molding, and bottle inspection, the preforms can be sterilized, hygienic bottles can be manufactured, and the beverages of the aforementioned hygienic bottles can be supplied to the aseptic filling line in an on-line mode.

Therefore, by applying the aforementioned stretch-blow molding in an on-site mode to an aseptic filling system for aseptic filling of polyester bottles such as PET bottles with beverages such as drinkable water, juices, tea, and coffee, it is possible to create very easily an aseptic filling system including the steps from bottle production to the aseptic filling of the bottles with beverages and sealing with sterilized caps.

INDUSTRIAL APPLICABILITY

In accordance with the present invention, a high bactericidal effect can be obtained even with respect to spore-forming bacteria by using a low-concentration sterilizing agent on the surface of a space and high safety with respect to human body and environment is attained. Therefore, a sterilization method can be achieved that can be realized with a simple and inexpensive spraying apparatus requiring no shielding. Such a method can be broadly applied to spaces that are required to be in hygienic state and preferred to be maintained in the hygienic state, such as a space where the equipment for production of containers such as hygienic bottles for aseptic filling with beverages and food or the production equipment in the production of medicines is present, a space relating to medicine, such as clinical equipment, nursing equipment, food stores and test rooms. Accordingly, the present invention has high industrial applicability.

The invention claimed is:

1. A method for sterilizing a surface of a space which is a space-to-be-sterilized of a container production equipment, comprising:

atomizing a sterilizing agent adjusted to a low concentration being any of an aqueous solution of hydrogen peroxide with a concentration of 1 to 10 wt %, an aqueous solution of peracetic acid with a concentration of 0.1 to 1 wt %, or an aqueous solution of hypochlorous acid with a concentration of 0.01 to 0.1 wt % at room temperature, making the sterilizing agent adhere to the surface of the space-to-be-sterilized with an adhered amount of 1 to 3 $mg/cm^2$, and then drying the sterilizing agent, wherein the drying of the sterilizing agent is performed by adjusting humidity from 20 to 60% RH and temperature of the space-to-be-sterilized from 25° C. to 50° C. and a drying time within a range of 5 to 60 minutes.

2. The method for sterilizing a surface of a space according to claim 1, wherein the sterilizing agent is atomized by mixing the sterilizing agent with air and spraying the mixture with an average particle size of 1 to 500 μm.

3. The method for sterilizing a surface of a space according to claim 1, wherein the sterilizing agent is dried under a positive-pressure atmosphere by blowing air.

4. The method for sterilizing a surface of a space according to claim 3, wherein the air used for drying the surface of the space-to-be-sterilized has been sterilized.

5. The method for sterilizing a surface of a space according to claim 1, wherein the surface of the space-to-be-sterilized is a surface of a product and equipment in a stretch-blow molding process of bottles.

6. The method for sterilizing a surface of a space according to claim 1, wherein the drying of the sterilizing agent is performed at a humidity between 20 to 60% RH and a temperature of the space-to-be-sterilized between 25° C. to 35° C.

7. The method for sterilizing a surface of a space according to claim 1, wherein the aqueous solution of hydrogen peroxide has a concentration of 1 to 5 wt %, the aqueous solution of peracetic acid has a concentration of 0.1 to 0.5 wt %, and the aqueous solution of hypochlorous acid has a concentration of 0.01 to 0.05 wt %.

8. The method for sterilizing a surface of a space according to claim 1, wherein the drying time is within a range of 20 to 60 minutes.

9. The method for sterilizing a surface of a space according to claim 8, wherein the drying time is within a range of 30 to 60 minutes.

* * * * *